United States Patent [19]
Simon

[11] Patent Number: 5,922,705
[45] Date of Patent: Jul. 13, 1999

[54] RAPID NARCOTIC DETOXIFICATION

[75] Inventor: David Lew Simon, Mansfield Center, Conn.

[73] Assignee: Intensive Narcotic Detoxification Centers of America, LLC, Tolland, Conn.

[21] Appl. No.: 09/059,031

[22] Filed: Apr. 13, 1998

Related U.S. Application Data

[63] Continuation-in-part of application No. 08/631,081, Apr. 12, 1996, Pat. No. 5,783,583.
[51] Int. Cl.$^6$ .................... A61K 31/55; A61K 31/515; A61K 31/44; A61K 31/08; A61K 31/05
[52] U.S. Cl. .................... 514/220; 514/270; 514/282; 514/289; 514/722; 514/731; 514/812
[58] Field of Search .................... 514/220, 270, 514/282, 289, 722, 731, 812

[56] References Cited

U.S. PATENT DOCUMENTS

| | | | |
|---|---|---|---|
| 3,896,226 | 7/1975 | Fishman | 424/260 |
| 4,535,157 | 8/1985 | Meltzer et al. | 546/44 |
| 4,987,136 | 1/1991 | Krook et al. | 514/282 |
| 5,272,149 | 12/1993 | Stalling | 514/255 |
| 5,783,583 | 7/1998 | Simon | 514/282 |
| 5,789,411 | 8/1998 | Goobermann et al. | 514/255 |

OTHER PUBLICATIONS

Partridge et al., "Pulmonary Edema Following Low-dose Naloxone Administration". Anesthesiology. vol. 65, No. 6. pp. 709–710. 1986.
Taff, "Pulmonary Edema Following Naloxone Administration in a Patient Without Heart Disease", Anesthesiology. 59. 576–77. 1983.
San et al, "High Risk of Ultrashort Noinvasive Opiate Detoxification". Am. J. Psychiatry 152. p. 956. Jun. 1995.
Brewer. C., Ultra–rapid, antagonist–precipitated opiate detoxification under general anesthesia or sedation. Addiction Biology 2/3, pp. 291–302, 1997.
Gerra et al., "Clonidine and Opiate Receptor Antagonists in the Threatment of Herion Addiction". Journal of Substance Abuse Treatment, vol. 12, No. 1. pp. 35–41. 1995.
Loimer et al., "Continuous Naloxone Administration Suppresses Opiate Withdrawel Symptoms In Huamn Opiate Addicts During Detoxification Treatment". 1989 pp. 81–86.
Text—*Opioid Peptides in Substance Abuse* by Jozsef I. Szekely. CRC Press, Inc., p. 160 (1994).
Article—Spanagel et al.—"Opposing tonically active endogenous opioid systems modulate the mesolimbic dopaminergic pathway" *Proc. Natl. Acad. Sci. USA* vol. 89. p. 2046. Mar. 1992.

Article—Pan et al. "Cellular mechanism for anti–analgesic action of agonists of the k–opioid receptor" *Nature* vol. 389/25 Sep., pp. 382–385.
Article—Kreeks et al. "Orally Administered opioid antagonists reverse mu and kappa opioid agonists delay of gastrointestinal transit in the guinea pig" *Life Sciences,* vol. 56. No. 14. pp. 1187–1192. 1995.
Article—Arts et al. "Inhibition of the Antianalgesic Action of Dynorphin A in Mice by Cholera Toxin" *Pharacology Biochemistry and Behavior,* vol. 46. pp. 623–629, 1993.
Article—Bakashi et al. "Dynorphin A–(1–17) Induces Alterations in Free Fatty Acids, Excitatory Amino Acids, and Motor Function Through An Opiate–Receptor–Mediated Mechanism" *The Journal of Neuroscience,* Dec. 1990. 10(12): 3793–3800.
Article—Behrmann et al. "A Comparison of YM–14673. U–50488H, and Nalmefene after Spinal Cord Injury in the Rat" *Experimental Neurology* 119. 258–267 (1993).
Article—Ohnishi et al. "Aquaretic Effect of the Stable Dynorphin–A analog E2078 in the Human" The Journal of Pharmacology and Experimental Therapeutics vol. 270. No. 1. Mar. 19, 1994.
Article—Sales et al. "[N–Methyl–Tyr$^4$–N–Methyl–Arg$^7$–D–LCU$^{8]}$—Dynorphin–A–(1–8)Ethylamide, a Stable Dynorphin Analog. Produces Diuresis by Kappa–Opiate Receptor Activation in the Rat" *The Journal of Pharmacology and Experimental Therapeutics* vol. 262. No. 3. 1992.
Article—Wang et al. "Contribution of Alpha–2 adrenoceptors to Kappa Opioid Agonist–Induced Water Diuresis in the Rat" *The Journal of Pharmacology and Experimental Therapeutics* vol. 270. 1994.
Article—O'Connor et al. Rapid and Ultrarapid Opioid Detoxification Techniques *JAMA*. Jan. 21, 1998—vol. 279. No. 3.
CA 112:229588, Koyuncuoglu et al., 1990.
CA 127:288090, Juvin et al., 1997.

*Primary Examiner*—Kimberly Jordan
*Attorney, Agent, or Firm*—Cummings & Lockwood

[57] ABSTRACT

Methods for rapid detoxification of patients addicted to opioid narcotics are provided. The methods include administering nalmefene to induce acute withdrawal, and administering dextromethorphan with nalmefene or other opioid antagonists to reduce the patient's subjective feelings of residual withdrawal symptoms following detoxification. In one method of rapid detoxification, unconsciousness is induced by anesthetizing the patient with desflurane.

9 Claims, No Drawings

RAPID NARCOTIC DETOXIFICATION

This application is a continuation in part of Ser. No. 08/631,081, filed Apr. 12, 1996, now U.S. Pat. No. 5,783,583.

FIELD OF INVENTION

The present invention relates to novel methods for rapid detoxification of patients addicted to opioid narcotics. In particular, the invention relates to such methods using opioid antagonists, such as nalmefene, and dextromethorphan and/or desflurane.

BACKGROUND OF THE INVENTION

Prior Art

An opiate is a remedy containing or derived from opium, Dordand's *Illustrated Medical Dictionary*, 26th edition. An opioid is any synthetic narcotic that has opiate-like activities but is not derived from opium, *Dorland's illustrated Medical Dictionary*, 26th edition. Either of said drugs may be classified as a narcotic. Many human beings are addicted to exogenous narcotics and want to become free of this addiction, but traditional withdrawal techniques result in high rates of dropout and early relapse. In order to improve the success of becoming free from addiction to exogenous narcotics, newer techniques have been promulgated which offer to lower the dropout rate from treatment and the relapse rate relating to failed treatment and further use of exogenous narcotics. In general, the process by which an addicted human being is ridded of the effects of an exogenous narcotic and undergoes the resultant process of withdrawal, is termed detoxification. Techniques for detoxification have been used whereby a narcotic antagonist is administered to a human being who is addicted to narcotics and currently using exogenous narcotics such that said narcotic antagonist displaces the exogenous narcotic from physiologic receptors in the body of the addicted human being, thus freeing up said exogenous narcotic from said receptors and allowing said exogenous narcotic to be excreted from the body by normal bodily mechanisms, as seen with LOIMER, LENZ et al., *American Journal of Psychiatry*, (1991), 148(7), 933–35. One of these techniques for detoxification involves the administration of the chemical compound (-)-17-Allyl-4,5alpha-epoxy-3,14dihydroxy=morphinan-6-one hydrochloride, known as naloxone, in conjunction with anesthesia, shown by LOIMER, HOFMANN, et al. *American Journal of Psychiatry*, (1993), 150(5), 839. Naloxone is used for this purpose because its salt preparation can be administered intravenously, but it is a bad drug for this purpose for two reasons: Firstly, it has a short chemical half-life in the human body so that its effects are too short-lasting, as shown in *NARCAN* package *insert*, @ 1995, Dupont Pharma; Secondly, it is associated with life-threatening adverse reactions, as shown by TAFT, *Anesthesiology*, (1983), 59, 576–77, and PARTRIDGE, et al., Anesthesiology, (1986), 65, 709–10, notably when used for the purpose of detoxification as indicated by SAN et al., *American Journal of Psychiatry*. (1995), 152, 956. A chemical compound related to naloxone in which the methyl group on the nitrogen atom is replaced by a cyclopropylmethyl group, known as naltrexone, has been used for this purpose by LEGARDA et al., Drug *Alcohol Depend* (1994), 35(2), 91–93, but it too has a major drawback: Naltrexone is known to cause hepatocellular injury, stated in *REVIA™ package insert*, ®1995, DuPont Pharma. Many human beings addicted to narcotics are at risk for abnormalities of liver function. Therefore, naltrexone is potentially very harmful to this group of human beings.

The chemical compound 17-(cyclopropylmethyl)-4,5alpha-epoxy-6-methylenemorphinian-3,14-diol, hydrochloride salt, known as nalmefene, may be used for detoxifying human beings addicted to narcotics in association with anesthesia because it is able to be administered intravenously, and because it does not cause hepatocellular injury as does naltrexone, shown by REVIA™ *package insert*, and REVEX™ *package* insert, April, 1995, Ohmeda Pharmaceutical Products Division, Inc. Also, because it is longer acting than naloxone, nalmefene is very favorable to naloxone for the purpose of rapid detoxification of narcotic addicts. Of all available narcotic antagonists, nalmefene is uniquely suited for the purpose of rapid narcotic detoxification. Despite this, nalmefene has not been used in published reports for the purpose of rapid narcotic detoxification, but naltrexone and naloxone have been used for this purpose in published reports. Nalmefene is not marketed by its manufacturer for narcotic detoxification, as evidenced by *REVEX™ package insert* Nalmefene's use as a drug for rapid detoxification is not obvious to its manufacturer or investigators in the field of narcotic detoxification. Nalmefene is not a new chemical compound.

The new, innovative use of a previous invention, that is, using nalmefene for rapid narcotic detoxification, is distinctly different from the proposed use of nalmefene as described by the distributing pharmaceutical company Ohmeda Pharmaceutical Products Division, Inc. In relation to use of nalmefene in patients physically dependent to narcotics, Ohmeda warns that nalmefene "is known to have the potential to produce acute withdrawal symptoms and therefore should be used with extreme caution in patients with known physical dependence on opioids." Furthermore and more definitively, the company specifically states that nalmefene "is contraindicated in patients with a known hypersensitivity to the product," as stated in REVEX™ *package insert* and REVEX™ (*nalmefene HCL injection*) *Product Monograph*, @ 1995, Ohmeda Pharmaceutical Division, Inc. By definition, a narcotic addict who is physically dependent upon exogenous opioids and who is currently using said exogenous opioids, is hypersensitive to nalmefene or other narcotic antagonists. Therefore, the company in charge of marketing nalmefene specifically warns against using it for the purpose of rapid detoxification, providing further evidence of the unobviousness of the present invention.

Nalmefene has been marketed for use in reversing respiratory depression and other effects of narcotic overdose. It is also marketed for reversing the respiratory depression sometimes seen with the administration of intrathecal narcotics. Nalmefene is not marketed for the purpose of detoxification. Naltrexone is marketed for use in treatment of alcoholism and for the long term treatment of human beings previously addicted to narcotics who have already undergone withdrawal and detoxification. Dupont Pharma, the pharmaceutical company which distributes naltrexone in the United states lists the following warning regarding naltrexone in capitalized letters: "DO NOT ATTEMPT TREATMENT WITH REVIA UNLESS, IN THE MEDICAL JUDGMENT OF THE PRESCRIBING PHYSICIAN, THERE IS NO REASONABLE POSSIBILITY OF OPIOID USE WITHIN THE PAST 7–10 DAYS," seen in *REVIA package insert*. Therefore, a reasonable physician would assume that naltrexone is not to be used for the purpose of inducing withdrawal as for detoxification. Nalmefene, which has come to market since the introduction of naltrexone, carries no information contrary to said warning for naltrexone.

Because nalmefene and naltrexone are both chemically related narcotic antagonists with similar pharmacological properties, a typical reasonable physician would assume that the same warning holds true for nalmefene as for naltrexone. Therefore, the present invention is not obvious to a typical reasonable physician.

Parenteral administration of a narcotic antagonist has been shown to produce a withdrawal syndrome which is different from the withdrawal syndrome following mere cessation of exogenous narcotic intake by virtue of the subsiding of symptoms in about two hours with said antagonist, as stated by GOODMAN et al., *Goodman and Gilman's The Pharmacological Basis of Disease,* (1980), 6th edition, 523–24. This is a significantly less amount of time for said symptoms to subside than without parenteral narcotic antagonist. This is very important because withdrawal from mere abstinence of exogenous narcotics without said narcotic antagonist can cause a prolonged and unpleasant withdrawal reaction for addicts which may last many days. The process can be shortened to 2–4 hours by administration of narcotic antagonists as shown by LEGARDA et al., and described by GOODMAN et. al. However, if said narcotic antagonists were medically administered to awake narcotic addicts, the symptoms would be unbearable or even life threatening. This is because human beings addicted to narcotics and currently using narcotics are hypersensitive to narcotic antagonists. This hypersensitivity is evidenced by the sympathetic nervous system becoming extremely excited when an addicted human being currently using narcotics is administered a narcotic antagonist. However, the unpleasant symptoms can be effectively masked by medically administering sedatives or anesthetics, and dangerous side effects can be attenuated by anesthesia. Therefore, a promising treatment for narcotic addiction is to place an addict in a state of unconsciousness and then to medically administer a narcotic antagonist. This results in a rapid, complete withdrawal process with minimal or no symptoms as shown by LEGARDA, et al., and PRESSLICH, et al., *Clinical Toxicology,* (1989), 27, 263–70, and LOIMER, SCHMIDT et al., *British Journal of Psychiatry,* (1988), 153. 851–52. However, when naloxone is used, it is necessary to use a constant infusion of naloxone because it is so short acting as evidenced by PRESSLICH et al., and LOIMER, SCHMIDT, et al. When a longer acting narcotic antagonist is infused over a short time, 2 hours for example, the effects of the longer acting narcotic antagonist are still present many hours after the infusion is discontinued. This is important because it is essential for detoxification that the effects of said narcotic antagonist are still in force after the human being regains consciousness after such a short amount of time undergoing withdrawal as embodied in the present invention. When an infusion of a shorter acting narcotic antagonist such as naloxone is discontinued, the effects of said shorter acting narcotic antagonist dissipate shortly thereafter. A shorter acting narcotic antagonist infusion, such as an infusion with naloxone, must therefore be infused for a much longer time. This would require greater utilization of resources for equipment and care by health workers, which increases the costs of delivering the treatment. Cost control is a major issue in health care delivery. Also, as seen by SAN et al., naloxone has been associated with very serious adverse effects when used in this way. Naltrexone is associated with hepatocellular injury. Of these three narcotic antagonists, namely naloxone, naltrexone and nalmefene, naltrexone is most noted for causing hepatocellular injury, which can be seen by reviewing the packages inserts of NARCAN, REVIA™ and REVEX™.

After the process of detoxification has been completed in a human being as described, said human being is typically prescribed a regimen of taking a narcotic antagonist orally in pill, tablet or capsule form for some time which improves abstinence from exogenous narcotics and decreases relapse rates to more use of exogenous opioids as shown by GERRA, et al., Journal of Substance Abuse and Treatment (1995), 12(1), 35–41.

STALLING, U.S. Pat. No. 5,272,149, relates to novel methods for the purpose of rapid detoxification, withdrawal and symptom management of addicted patients. However, STALLING's method is needlessly complicated and complex. He states that first an autonomic nervous system blocking agent be administered, followed by a short-acting narcotic antagonist, followed by a combination narcotic agonist-antagonist, in a repeating fashion and so forth over many hours. His method is tedious, cumbersome and unnecessary. Furthermore, it takes many times longer to accomplish detoxification than with the present invention. In addition, STALLING's method includes multiple urinalysis examinations over the course of the procedure. These urinalysis examinations clearly are not needed and they represent a waste of resources. The present invention presents a way of achieving rapid narcotic detoxification in significantly less steps, which can be accomplished is less time and at less expense. STALLING's invention, while being unnecessarily complicated and complex, is also too vague: He describes administering an autonomic nervous system blocking agent, but he does not describe whether the sympathetic portion of the autonomic nervous system should be blocked or the parasympathetic portion of said autonomic nervous system. This is an important distinction. The present invention does not necessarily require a specific autonomic nervous system blocking agent because anesthesia or significant sedation is known to attenuate the excited response of the sympathetic nervous system. Anesthesia or significant sedation given during rapid detoxification greatly alleviates what would otherwise be an excruciating process, that is, medically administering a narcotic antagonist to a patient addicted to narcotics who is currently using exogenous narcotics. Anesthesia or significant sedation must be given for detoxification over such a short period of time as part of a humane and compassionate treatment because the withdrawal response precipitated by the narcotic antagonist is so severe. Importantly, STALLING's method does not include the use of 17(cyclopropylmethyl)-4,5alpha-epoxy-6-methylenemorphinan-3,14-diol, hydrochloride salt, also known as nalmefene. STALLING's method, if followed step by step, would have to take much longer than the present invention, and this would result in much greater costs incurred.

FISHMAN, U.S. Pat. No. 3,896,226 claims 6-methylene-6-desoxy dihydro morphine and codeine derivatives and pharmaceutically acceptable salts thereof as a narcotic antagonist composition. However, there are different uses for narcotic antagonists and FISHMAN makes the argument for using his invention as one which "could be administered orally in comparatively small doses." He does state that another object of his invention is to provide a narcotic antagonist which is also capable of being administered parenterally. However, for the purpose of rapid detoxification, it is not enough to simply claim the invention as a narcotic antagonist. FISHMAN states "It thus will be seen that there have been provided compositions and methods for narcotic antagonists which accomplish the various objects of the invention and are well adapted to meet the conditions of practical use." In fact, on Jul. 22, 1975, the date of issue for U.S. Pat. No. 3,896,226, it was not practical to perform rapid narcotic detoxification as claimed in the present invention because the general knowledge necessary for this process was not available then. The references provided herein relating to rapid detoxification from narcotics go back only as far as 1980. More importantly, in order for rapid narcotic detoxification to be performed safely as embodied in the present invention, current standards of anesthesia practice must be adhered to. These standards of practice include the use of pulse oximetry and capnography. The state of technology in 1975 did not make it practical to use pulse oximetry and capnography as is presently used. Pulse oximetry and capnography were not readily available nor where they considered the standard of practice in anesthesia care in 1975. Therefore, it was not practical in 1975 to use nalmefene as embodied in the present invention. FISHMAN's invention as embodied in U.S. Pat. No. 3,896,226 may have been well adapted to meet the conditions of practical use in 1975, but conditions of practical use are different in 1996 than they were in 1975. Therefore, FISHMAN's claims for his said invention do not apply to the present invention which represents a practical and novel use of a previous invention pertaining to current conditions. FISHMAN's claims could only possibly relate to what was practical in 1975, and what is practical in 1996 as relating to the present invention was not practical in 1975. MELIZER, et al, U.S. Pat. No. 4,535,157 relates to an improved process for the manufacture of the chemical compound embodied in the present invention and does not relate to the new, practical and novel use of said compound as embodied in the present invention.

OBJECTS AND ADVANTAGES

Accordingly, besides the objects and advantages of using nalmefene for rapid narcotic detoxification as described above, some objects and advantages of the present invention are:

(a) to use a narcotic antagonist to detoxify a narcotic addict in a short amount of time;

(b) to medically administer a long acting narcotic antagonist intravenously which increases the practicality and safety of drug administration during rapid narcotic detoxification;

(c) to decrease the likelihood of liver damage by virtue of the fact that nalmefene does not cause hepatocellular damage to the degree that other narcotic antagonists do;

(d) to administer a narcotic antagonist over a short period of time while allowing for its effects to be long-lasting whereby a constant infusion of narcotic antagonist over a long period of time is not needed;

(e) to avoid severe and life threatening complications, such as pulmonary edema, as is seen with other narcotic antagonists;

(f) To allow for the easy continuation of administering narcotic antagonists in oral tablet, capsule or pill form to a human being after he undergoes the detoxification process, which is accomplished by administering a long-acting narcotic antagonist for a short time during the detoxification process, which allows for easy conversion to oral therapy later on;

(g) To improve drug addiction treatment, enhance abstinence from narcotics and to decrease relapse rate to recurrent drug use.

Still further objects and advantages will become apparent from a consideration of the ensuing description.

DESCRIPTION OF THE INVENTION

The present invention is comprised of producing a state of unconsciousness in a human being who is addicted to and currently using exogenous narcotics, monitoring the life functions of said human being in accordance with acceptable standards of anesthesia practice, and administering a narcotic antagonist, preferably nalmefene, such that a withdrawal reaction will be precipitated in said human being that will last a short time, such that said unconscious human being will not consciously be aware of experiencing, or having had experienced, the withdrawal process.

EXAMPLE 1

A narcotic addict will undergo intravenous cannulation by either the peripheral or central venous route, and the appropriate intravenous solution will be infused intravenously at the appropriate rate for the size and conditions of the patient. Usual anesthetic monitoring techniques are employed. A medication to induce unconsciousness will be administered, preferably by the intravenous route, in doses appropriate for said human being's weight and medical condition. This medication should be a nonopioid derivative not related to the narcotic classification of drugs. Such a drug may be midazolam, propofol, sodium pentothal, a combination thereof, or other drugs commonly used to induce unconsciousness. Once unconsciousness is achieved, and after stabilization of life function, nalmefene may be administered via the intravenous route. Administration may be preceded by intravenous naloxone in a fashion commonly referred to as a "naloxone challenge," though this step is not absolutely necessary. A naloxone challenge may be administered prior to administration of nalmefene to ascertain whether or not said human being is addicted to narcotics. Another reason for performing a naloxone challenge is because naloxone is expected to exert similar changes in life function to said human being as is nalmefene, but the effects of naloxone are much shorter acting than nalmefene, so if there is an adverse reaction to a narcotic antagonist, the effects of naloxone administration will dissipate more quickly that the effects after nalmefene administration would. After administration of nalmefene, said human beings life functions are monitored until it becomes apparent to the treating physician that the withdrawal reaction has subsided. Evidence of withdrawal may be expected to subside two to six hours after administration of narcotic antagonist. After evidence of withdrawal has subsided, said human being is allowed to regain consciousness. Upon awakening, the acute phase of withdrawal is over and said human being is detoxified from the previously abused exogenous narcotic.

EXAMPLE 2

A narcotic addict will undergo intravenous cannulation by either the peripheral or central venous route, and the appropriate intravenous solution will be infused intravenously at the appropriate rate for the size and conditions of the patient. Monitors of life function shall be attached to the patient which may include a pulse oximeter, electrocardiogram patches, a blood pressure cuff attached to a sphygmomanometer and a means to measure the carbon dioxide of said addict's exhaled breath by way of capnography. A medication to induce unconsciousness will be administered, preferably by the intravenous route, in doses appropriate for said human being's weight and medical condition. This medication should be a nonopioid derivative not related to the narcotic classification of drugs. Such a drug may be midazolam, propofol, sodium pentothal, a combination thereof, or other drugs commonly used to induce unconsciousness. A dose of 0.3 milligrams of midazolam per kilogram of said addict's weight administered intravenously may be sufficient to produce unconsciousness. This may be followed by intravenous administration of a medication such as a depolarizing or non-depolarizing neuromuscular blocking agent to facilitate intubation of said addict's trachea. The endotracheal tube is then secured in the correct anatomic position using usual anesthetic care measures. After stabilization of said addict's life functions as usually done in routine anesthetic management, the patient may be administered nalmefene, by continuous intravenous infusion. For a 70 kilogram adult male, the typical initial rate of said nalmefene infusion would consist of infusing 1.5 milligrams of nalmefene over two hours. Said infusion rate of nalmefene may be titrated upward or downward depending on the response of said addict's sympathetic nervous system as evidence by monitoring of life functions and other clinical criteria. After two hours, the nalmefene infusion would typically be discontinued. Some time thereafter, usually no more than four hours after said infusion of nalmefene is complete, the patient can be expected to be detoxified and can be safely rendered back to a state of consciousness. Upon awakening the acute phase of withdrawal will have been completed.

EXAMPLE 3

A narcotic addict will undergo intravenous cannulation by either the peripheral or central venous route, and the appropriate intravenous solution will be infused intravenously at the appropriate rate for the size and conditions of the patient. Monitors of life function shall be attached to the patient which may include a pulse oximeter, electrocardiogram patches, a blood pressure cuff attached to a sphygmomanometer and a means to measure the carbon dioxide of said addict's exhaled breath by way of capnography. A medication to induce unconsciousness will be administered, preferably by the intravenous route, in doses appropriate for said human being's weight and medical condition. This medication should be a nonopioid derivative not related to the narcotic classification of drugs. Such a drug may be midazolam, propofol, sodium pentothal, a combination thereof, or other drugs commonly used to induce unconsciousness. Typically, 3–5 mg of sodium pentothal per kilogram of said addict's weight could be administered for this purpose of producing unconsciousness. This may be followed by administration of a neuromuscular junction blocking agent to facilitate intubating said addict's trachea, though said neuromuscular junction blocking agent may not be necessary. If a neuromuscular junction blocking agent is used, it is preferable to use a short-acting agent such that signs of motor agitation and piloerection are not masked during the detoxification procedure. The endotracheal tube is then secured in the correct anatomic position using usual anesthetic care measures. After stabilization of said addict's life functions as usually done in routine anesthetic management, the patient may be administered nalmefene in small incremental intravenous bolus doses as determined by the physician's interpretation of the response of said addict's monitored life functions and other clinical parameters, up to a maximum dose of 1.5–2.0 milligrams for a 70 kilogram adult male. The end point of nalmefene-induced narcotic detoxification can be considered when said addict appears to have no further evidence of acute withdrawal after at least 0.5 to 1.5 milligrams of nalmefene have been given over a short period of time. Said other clinical parameters may include looking for the following clinical signs: mydriasis, vomiting, motor agitation, lacrimation, rhinorrhea, diaphoresis and piloerection. Life functions include but are not limited to blood pressure and heart rate.

To reduce a patient's subjective feelings of residual withdrawal symptoms following detoxification, often referred to colloquially as "dope sickness", dextromethorphan is administered prior to the detoxification procedure as a pretreatment or during the detoxification procedure. It should be understood that the use of dextromethorphan for this particular purpose is not limited to a rapid detoxification procedure using nalmefene, but also applies in detoxification procedures which utilize naloxone, naltrexone or other opioid antagonists to induce an acute withdrawal reaction.

In the case where dextromethorphan is administered as a pretreatment, the patient may be given the drug up to several hours, typically about two hours, prior to the detoxification procedure. Preferably, the dextromethorphan is administered orally as a pre-treatment. Where dextromethorphan is administered during the detoxification procedure, the drug is given immediately prior to, at the same time or immediately after the patient receives the opioid antagonist. Preferably, dextromethorphan is administered to the stomach via an orogastric or nasogastric tube.

Typically, dextromethorphan is administered in a dosage range of from about 0.3 to about 0.7 mg/kg of body weight, although the dosage for a particular patient may vary depending on a number of clinical criteria including, the amount and duration of the patient's opioid abuse and recognized genetic differences among patients in the manner in which they react to particular drugs. The preferred dosage is about 0.5 mg/kg of body weight, and the preferred dosage form is a sustained release dextromethorphan formulation such as the sustained release liquid formulation DELSYM® available from Medeva Pharmaceuticals, Inc of Fort Worth Texas.

To further aid the patient in coping with post-detoxification residual withdrawal symptoms, dextromethorphan dosing is continued after the detoxification procedure is complete. Dosages are, again, in the range of from about 0.3 to about 0.7 mg/kg of body weight but may be varied depending not only on the above-mentioned factors, but also on additional factors including the severity of the post-detoxification withdrawal symptoms, and the degree to which the patient is coping with the withdrawal symptoms based on a given dosage of dextromethorphan. The preferred dosage is 0.5 mg/kg of body weight administered every six to twelve hours until the patient's subjective feelings of residual withdrawal symptoms have passed. The most preferred dosage for postdetoxification treatment is the sustained release DELSYM® formulation noted above, dosed every twelve hours.

EXAMPLE 4

A narcotic addicted patient undergoes intravenous cannulation by either the peripheral or central venous route, and the appropriate intravenous solution is infused intravenously at the appropriate rate for the size and conditions of the patient. Monitors of life function are attached to the patient which include a pulse oximeter, electrocardiogram patches, a blood pressure cuff attached to a sphygmomanometer and a means to measure the carbon dioxide of the patient's exhaled breath by way of capnography. A medication to induce unconsciousness is administered, preferably by the intravenous route, in doses appropriate for the patient's weight and medical condition. This medication should be a nonopioid derivative not related to the narcotic classification of drugs. Such a drug may be midazolam, propofol, sodium pentothal, a combination thereof, or other drugs commonly used to induce unconsciousness. Typically, 3–5 mg of sodium pentothal per kilogram of said addict's weight is administered for the purpose of producing unconsciousness. This is followed by administration of a neuromuscular junction blocking agent to facilitate intubating the patient's trachea, though said neuromuscular junction blocking agent may not be necessary. If a neuromuscular junction blocking agent is used, it is preferable to use a short-acting agent such that signs of motor agitation and piloerection are not masked during the detoxification procedure. The endotracheal tube is then secured in the correct anatomic position using usual anesthetic care measures. After stabilization of the patient's life functions as usually done in routine anesthetic management, the patient is administered 0.3 to 0.7 mg/kg of dextromethorphan *per os,* as through an orogastric tube. The patient is then administered nalmefene in small incremental intravenous bolus doses as determined by the physician's interpretation of the response of the patient's monitored life functions and other clinical parameters, up to a maximum dose of 1.5–2.0 milligrams for a 70 kilogram adult male. The end point of nalmefene-induced narcotic detoxification can be considered when the patient appears to have no further evidence of acute withdrawal after at least 0.5 to 1.5 milligrams of nalmefene have been given over a short period of time. This period is typically from about two to about six hours after the administration of the nalmefene. The other clinical parameters may include looking for the following clinical signs: mydriasis, vomiting, motor agitation, lacrimation, rhinorrhea, diaphoresis and piloerection. Life functions include but are not limited to blood pressure and heart rate. After awakening from the anesthesia, the patient is administered 0.5 mg/kg of dextromethorphan every 6 to 12 hours until the subjective feelings of residual withdrawal symptoms have passed.

As noted above, a number of drugs for inducing unconsciousness may be utilized, provided that the medication selected should be a nonopioid derivative not related to the narcotic classification of drugs. However, once unconsciousness has been induced, it has been found that desflurane is particularly useful as an anesthetic agent for maintaining anesthesia during rapid detoxification procedures using nalmefene, naloxone, naltrexone or other opioid antagonists to precipitate the acute withdrawal reaction. Desflurane decreases the recovery time from anesthesia and permits earlier ambulation following anesthesia. Moreover, desflurane, at normal anesthetic and sub-toxic doses produces an isoelectric electroencephalogram (EEG). A condition specific to detoxification, without regard to the particular opioid antagonist used, and which is not usually encountered in routine anesthesia such as, for example, surgery, is that detoxification may be associated with brain electrical seizure activity. By producing an isoelectric EEG at doses which safely render unconsciousness, desflurane prevents any electrical seizure activity during the acute withdrawal/detoxification process under anesthesia. This is of great clinical significance because anesthesia may, in some cases, mask the manifestations of brain seizure activity. If a patient were to have a prolonged seizure which was not recognized and halted with appropriate medical treatment, for instance during the two to about six hours or so of rapid detoxification under anesthesia, this could result in potentially serious and harmful effects.

After unconsciousness has been induced in the patient, desflurane is preferably administered in the rapid detoxification procedure as a volatile anesthetic agent which is inhaled by the patient through the respiratory tract, the lungs and/or the capillaries of alveoli in the lungs. Desflurane is administered at a dose which readily allows for spontaneous respiration. This dose is measured as the mean alveolar concentration (MAC), which, for a particular volatile anesthetic agent, is the dosage at which 50% of patients do not respond to a surgical stimulus. The MAC for desflurane varies significantly with age. However, in general, the alveolar concentration of desflurane which is preferable for the majority of patients undergoing rapid narcotic detoxification under anesthesia varies from about 5.5% to about 8.5% expressed in terms of percent of barometric pressure due to the presence of desflurane.

EXAMPLE 5

A patient addicted to narcotic will undergo intravenous cannulation by either the peripheral or central venous route, and the appropriate intravenous solution is infused intravenously at the appropriate rate for the size and conditions of the patient to produce initial unconsciousness. Monitors of life function are attached to the patient which may include a pulse oximeter, electrocardiogram patches, a blood pressure cuff attached to a sphygmomanometer and a means to measure the carbon dioxide of the patient's exhaled breath by way of capnography. Desflurane is administered via inhalation, as through an endotracheal tube, at an alveolar concentration ranging from about 5.5% to about 8.5%. This may be accompanied by intravenous administration of a medication such as a non-depolarizing neuromuscular blocking agent. After stabilization of the patient's life functions as usually done in routine anesthetic management, and adjustment of the dose of desflurane as in routine anesthetic management, the patient is administered nalmefene by continuous intravenous infusion. For a 70 kilogram adult male, the typical initial rate of the nalmefene infusion would consist of infusing 1.5 milligrams of nalmefene over two hours. The infusion rate of nalmefene may be titrated upward or downward depending on the response of the patient's sympathetic nervous system as evidence by monitoring of life functions and other clinical criteria. Some time thereafter, usually no more than from about two to about six hours after the administration of nalmefene, the patient can be expected to be detoxified and can be safely rendered back to a state of consciousness, by discontinuing the administration of desflurane. Upon awakening the acute phase of withdrawal will have been completed.

As noted above, dextromethorphan has proven effective in reducing a patient's subjective feelings of residual withdrawal symptoms following rapid detoxification. The effectiveness of dextromethorphan for this purpose does not depend on the particular opioid antagonist used to precipitate the acute withdrawal reaction. This is also the case with respect to the use of desflurane to maintain anesthesia during rapid detoxification. Accordingly, dextromethorphan may be used as discussed above in a rapid detoxification procedure in which desflurane is also used to maintain anesthesia.

What is claimed is:

1. A method for detoxifying a patient who is addicted to and who is currently using exogenous narcotics, said method comprising the steps of:

(a) anesthetizing the patient to produce a state of unconsciousness;

(b) administering nalmefene to detoxeify the patient; and (c) allowing the patient to regain consciousness after about 2 to about 6 hours following the administration of the nalmefene.

2. The method of claim 1, wherein the nalmefene is administered intravenously.

3. The method of claim 2, wherein the nalmefene is administered by intravenous infusion.

4. The method of claim 2, wherein the nalmefene is administered by incremental intravenous bolus doses.

5. The method of claim 2, wherein the nalmefene is administered intravenously over of period of about two hours.

6. The method of claim 1, wherein step (b) is further characterized in that the nalmefene is administered in an amount ranging from about 0.5–1.5 mg to no more than about 1.5–2.0 mg based on the weight of a 70 kg adult male.

7. The method of claim 1, wherein the step (a) is further characterized in that the patient is anesthetized by administering a non-opioid derivative to the patient.

8. The method of claim 7, wherein the non-opioid derivative is selected from the group consisting of midazolam, propofol, sodium pentathal and combinations thereof.

9. The method of claim 1, wherein prior to step (b) the method further comprises the step of administering naloxone to the patient to perform a naloxone challenge.

* * * * *